United States Patent [19]

Hedge et al.

[11] Patent Number: 4,904,644

[45] Date of Patent: Feb. 27, 1990

[54] **ANTIMICROBIAL COMPOUND ISOLATED FROM *ACTINOMADURA FULVA* SUBSP INDICA**

[75] Inventors: Vinod R. Hedge, Rockaway; Ann C. Horan, Summit; Arthur H. King, East Orange; Frank A. Gentile, Wayne; Mahesh G. Patel, Verona; Gerald H. Wagman, East Brunswick, all of N.J.

[73] Assignee: Schering Corporation, Kenilworth, N.J.

[21] Appl. No.: 227,963

[22] Filed: Aug. 3, 1988

[51] Int. Cl.$^4$ .................. A61K 31/71; C07H 17/08
[52] U.S. Cl. .................................. 514/29; 536/17.4; 536/18.7; 435/75; 435/825
[58] Field of Search .............. 536/17.4, 18.7, 7.4; 435/75; 514/29

[56] References Cited

U.S. PATENT DOCUMENTS 4,518,590  5/1985  Hauske et al. .................... 536/7.4

FOREIGN PATENT DOCUMENTS 18035  4/1984  Japan.

*Primary Examiner*—Herbert J. Lilling
*Assistant Examiner*—Elli Peselev
*Attorney, Agent, or Firm*—Thomas D. Hoffman; Gerald S. Rosen

[57] ABSTRACT

A macrolactam disaccharide isolated from an antimicrobial complex 530 produced in fermentation under controlled conditions using a biologically pure culture of the microorganism *Actinomadura fulva* subsp. indica ATCC 53714.

12 Claims, No Drawings

ANTIMICROBIAL COMPOUND ISOLATED FROM *ACTINOMADURA FULVA* SUBSP INDICA

This invention relates to a macrolactam disaccharide antimicrobial compound. The compound is isolated from an antimicrobial complex 530 which is produced in fermentation under controlled conditions using a biologically pure culture of the microorganism, *Actinomadura fulva* subsp. *indica* SCC 1840, ATCC 53714.

CROSS REFERENCE TO RELATED APPLICATIONS

In a related, commonly assigned, co-pending application Ser. No. 227,964, filed on Aug. 3, 1988, three novel macrolactam monosaccharides produced by fermentation of *A. fulva* subsp. *uruguayensis* ATCC 53713 are disclosed.

In another related, commonly-assigned, co-pending application Ser. No. 227,968 filed on Aug. 3, 1988, a novel macrolactam monosaccharide produced by fermentation of *A. vulgaris* subsp. *vulgaris* sp nov, ATCC 53748 are disclosed.

In another related, commonly-assigned co-pending application Ser. No. 227,951 filed on, Aug. 3, 1988, a novel macrolactam monosaccharide produced by fermentation of *A. vulgaris* subsp. *lanata* ATCC 53715 is disclosed.

SUMMARY OF THE INVENTION

The present invention embraces *Actinomadura fulva* subsp. *indica* SCC 1840, ATCC 53714 and mutants and variants thereof having the identifying characteristics of *Actinomadura fulva* subsp. *indica*.

Another aspect of the present invention is directed to the antimicrobial complex 530 produced by cultivating a strain of *Actinomadura fulva* subsp. *indica* SCC 1840 having the identifying characteristics of ATCC 53714 in a pH and temperature controlled medium having assimilable sources of carbon and nitrogen under controlled submerged aerobic conditions until a composition of matter having substantial antimicrobial activity is produced.

The present invention is also directed to a component of the antimicrobial complex 530, i.e. a compound represented by the formula 1:

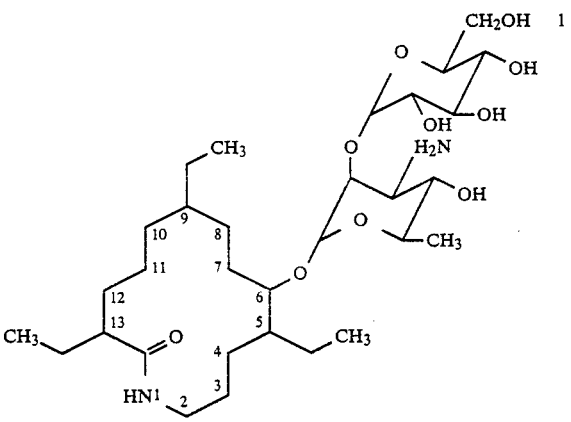

in substantially chemically pure form, or a pharmaceutically acceptable salt thereof.

The present invention also contemplates the mono to hexa ($C_1$-$C_{22}$) alkanoyl and ($C_3$-$C_{22}$) alkenoyl derivatives of the compound represented by formula 1, i.e., compounds represented by formula 2:

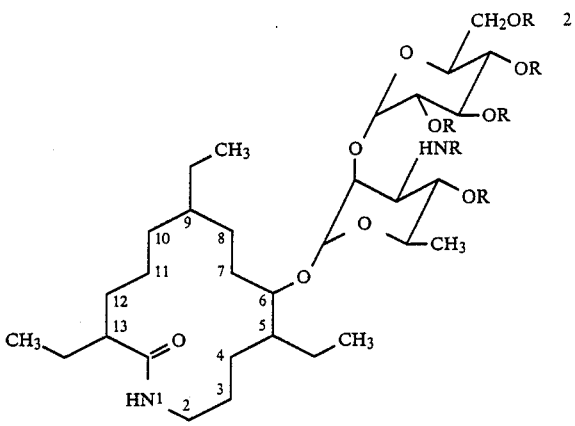

wherein R is a straight or branched chain ($C_1$-$C_{22}$) alkanoyl group, a straight or branched chain ($C_3$-$C_{22}$) alkenoyl group or hydrogen, with the proviso that at least one R is not hydrogen, or a pharmaceutically acceptable salt thereof.

THE MICROORGANISM

The microorganism used for the production of antimicrobial complex 530 and the compound represented by formula 1 is a biologically pure culture of *Actinomadura fulva* subsp. *indica* subsp. nov. SCC 1840, ATCC 53714.

A viable culture of this microorganism has been deposited in the collection of the American Type Culture Collection (ATCC) in Rockville, Md., where it has been assigned accession number ATCC 53714. Should the deposited culture become lost, destroyed or non-viable during the longer of the thirty (30) year period from the date the culture was deposited or the five (5) year period after the last request for the deposited culture or the effective life of the patent which issues from this application, the culture will be replaced upon notice by applicants or assignee(s) of this application. Subcultures of *Actinomadura fulva* subsp. *indica* SCC 1840, ATCC 53714 are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the US Patent Laws.

The microorganism was isolated from a sample of soil collected in India. It had been characterized and found to have the microscopic, macroscopic, and whole cell hydrolysis properties of the genus Actinomadura.

DESCRIPTION OF THE PRODUCING STRAIN: *ACTINOMADURA FULVA* SUBSP. *INDICA* SCC 1840, ATCC 53714

Source material for the following taxonomic evaluations was a frozen preparation of a pure culture of *Actinomadura fulva* subsp. *indica* SCC 1840, ATCC 53714. Inoculum for the biochemical and physiological tests was prepared according to the procedures of Horan and Brodsky [Horan and Brodsky, *Int. J. Syst. Bacteriol.*, Vol. 32, pp. 195-200 (1982)]. The incubation temperature for the biochemical and physiological tests was 30°

C. Readings of the results were made at various times up to 21 days for the plate media. Most of the tubed media were read at various times up to 28 days. The tests for decomposition of urea, allantoin and hippurate, as well as the tests for the reduction of nitrates were read for six weeks.

MORPHOLOGY

Morphological observations of the producing strain of the microorganism of this invention were made on plates of water agar, AV-agar [Nonomura and Ohara, *J. Ferment. Technol.*, Vol. 47, pp. 463–469 (1966)] or modified inorganic salts-starch agar [Difco inorganic salts-starch agar (ISP-4), 12 g; Difco Bacto agar, 15 g; distilled water, 800 ml; soil extract 200 ml; thiamine HCL, 0.5 mg; riboflavin, 0.5 mg; niacin, 0.5 mg; pyridoxine HCL, 0.5 mg; inositol, 0.5 mg; calcium pantothenate, 0.5 mg; p-aminobenzoic acid, 0.5 mg; biotin, 0.25 mg]. Plates were incubated at 30° C. and observed for 4 to 6 weeks.

The producing strain of the microorganism of this invention is a gram positive, filamentous organism that forms a well-developed substrate mycelium with non-fragmenting, moderately branching hyphae which are approximately 0.4 $\mu$m to 0.8 $\mu$m in diameter. There are no spores on the substrate mycelium.

The aerial hyphae, approximately 0.4 $\mu$m to 0.9 $\mu$m in diameter, bear chains of smooth-walled spores. The spores are round to ovoid and approximately 0.9 t 1.5 $\mu$m in diameter. The spore chains contain approximately 6 to 33 spores per chain and are arranged in tightly appressed spirals forming pseudosporangia. The pseudosporangia are approximately 2 to 7 $\mu$m in diameter. No motile elements were observed in either the substrate or aerial mycelium.

CHEMOTAXONOMY

Purified cell wall preparations of the producing strain of this invention were analyzed by the method of Becker [Becker et al., *Appl. Microbiol.*, Vol. 12, pp. 421–423 (1964)] and shown to contain the mesoisomer of 2,6-diaminopimelic acid, alanine, glutamic acid, glucosamine, muramic acid and traces of mannose. Whole-cell hydroysates were analyzed by the method of Lechevalier [Lechevalier, M. P., *J. Lab. Clin. Med.*, Vol. 71, pp. 934–944 (1968)] and shown to contain glucose, mannose, madurose, ribose, a trace of galactose and a trace of rhamnose. The phospholipids present are diphosphatidylglycerol, phosphatidylinositol, phosphatidylethanolamine, and unknown glucosamine containing phospholipids. Thus, the producing strain of the microorganism of this invention has a type III cell wall with a type B whole-cell sugar pattern and a type P IV phospholipid composition [Lechevalier et al., *Biochem. System. Ecol.*, Vol. 5, pp. 249–260 (1977)], typical of actinomadurae.

PHYSIOLOGICAL AND BIOCHEMICAL CHARACTERISTICS

The procedures used to obtain the captional characteristics were those cited by Gordon [Gordon, R. E., *J. Gen. Microbiol.*, Vol. 45, pp. 355–364 (1966)], Luedemann and Brodsky [Luedemann and Brodsky, "*Antimicrob. Agents Chemother.*" pp. 47–52 (1965)] and Horan and Brodsky [Horan and Brodsky, *Int. J. Syst. Bacteriol.*, Vol. 32, pp. 195–200 (1982)]. The producing strain of the microorganism of this invention, SCC 1840, produces acid from adonitol, D-arabinose, L-arabinose, D-fructose, L-fucose, D-galactose, glucose, glycerol, i-inositol, maltose, D-mannitol, D-mannose, $\alpha$-D-melibiose, $\alpha$-methyl-d-glucoside, $\beta$-methyl-D-glucopyranoside, $\alpha$-L-rhamnose, D-ribose, sucrose, D-trehalose and D-xylose but not from dulcitol, i-erythritol, D-melizitose, or D-sorbitol. Adenine, hypoxanthine, L-tyrosine, elastin, casein and hippurate are hydrolyzed but guanine, xanthine, xylan and chitin are not. Gelatin is both hydrolyzed and liquified. Starch hydrolysis is negative. Urease is formed; allantoinase is not. Nitrate is reduced to nitrite. Melanin and hydrogen sulfide are formed. Growth does not occur at 10° C. or at 45° C. Growth is fair at 40° C. The microorganism of this invention, SCC 1840, grows poorly at 4% NaCl; good growth occurs at 3% NaCl. Acetate, butyrate, lactate, pyruvate and succinate are utilized; but benzoate, formate, oxalate and tartrate are not.

The producing strain of the microorganisms of the present invention grows in the presence of 50 $\mu$g/ml of kanamycin, streptomycin, novobiocin, rifamycin, erythromycin, penicillin G, cephalothin, tetracycline, cycloserine and spectinomycin and in the present of 10 mcg/ml of neomycin. Growth is poort in the presence of 50 mcg/ml of sisomicin, gentamicin and clindamycin.

DESCRIPTION OF *A. FULVA* SUBSP. *INDICA* ON VARIOUS MEDIA

All plates were incubated at 30° C. and observed at intervals up to 28 days. The common names for the colors were choosen after comparison with color chips from the ISCC-NBS centroid color charts, the "*Color Harmony Manual*", Ed. 4 (Container Corp. America, 1958), or the "*Methuen Handbook of Color*" (Eyre Methuen, London, 1981). On all media tested, the substrate mycelium of the microorganism of this invention, SCC 1840, was off-white, yellow-brown or brown. The aerial mycelium was white, yellowish white or ivory. Yellow-brown diffusible pigments were formed. Characteristics are presented in Table 1.

On the basis of its morphological and chemotaxonomic characteristics, the producing strain of of this invention, SCC 1840, was placed in the genus Actinomadura. The description of the microorganism of this invention, SCC 1840, was compared to the descriptions of Actinomadura species found on the approved lists of bacterial names or in the patent literature. The microorganism of this invention SCC 1840 was found to resemble the descriptions of *Actinomadura fulva* and was therefore compared to *A. fulva* Ferm-P3683 disclosed by A. Tamura and A. Tanaka (Dainippon) in Japanese Patent Publication No. 18035, published Apr. 25, 1984, based on Japanese Kokai 78-28,101, published Mar. 16, 1978 as well as *A. fulva* subsp. *uruguayensis* SCC 1778, ATCC 53713 disclosed in commonly-owned, co-pending application.

All three cultures are similar in morphology and growth characteristics on various media. All form a substrate mycelium which varies from off-white through yellow to yellow-brown and brown. Both *A. fulva* Ferm-P3683 and the microorganism of this invention, SCC 1840, form a white, yellowish white or ivory aerial mycelium. *A. fulva* subsp. *uruguayensis* SCC 1778, ATCC 53713 tends to form very sparse aerial mycelia, but when visible it is white. The aerial mycelium of all three organisms produce chains of smooth-walled spores which are arranged in tightly appressed spirals forming distinct pseudosporangia. All three microorganisms form only yellow-brown diffusible pigments.

*A. fulva* Ferm-P3683 differs from the microorganism of this invention SCC 1840 in that *A. fulva* Ferm-P3683 fails to produce acid from L-arabinose and β-methyl-d-glucopyranoside, does form allantoinase and grows in the presence of 50 μg/ml of neomycin. The microorganism of this invention, SCC 1840, is therefore considered to represent a subspecies of *A. fulva*.

The microorganism of this invention, SCC 1840, produces a more abundant aerial mycelium on a wider variety of media than does *A. fulva* subsp. *uruguayensis* ATCC 53713. SCC 1840 also produces acid from L-arabinose and hydrolyses urea and hippurate while ATCC 53713 does not. SCC 1840 is considered therefore to be a distinct new subspecies of *A. fulva* designated *A. fulva* subsp. *indica*.

TABLE 1

Macroscopic Appearance of *Actinomadura fulva* susp. indica SCC 1840, ATCC 53714 on various descriptive media[a]

| MEDIUM | RESULT |
|---|---|
| Yeast Extract- Malt Extract Agar (ISP 2) | G: good to excellent<br>AM: present; abundant, white to ivory (CHM 2db)<br>SC: numerous<br>DFP: present; pale yellow-brown<br>SMP: yellow-brown to grayish brown (ISCC-NBS 61) |
| Oatmeal Agar (ISP 3) | G: fair<br>AM: present; sparse to moderate, white to off-white<br>SC: numerous<br>DFP: present; pale yellow-brown<br>SMP: off-white to moderate brown (ISCC-NBS 58) |
| Inorganic Salts Starch Agar (ISP 4) | G: fair<br>AM: present; moderate, white<br>SC: numerous<br>DFP: absent<br>SMP: yellow (CHM 2fb, pastel yellow) to yellow-brown |
| Glycerol-Asparagine Agar (ISP 5) | G: good<br>AM: present; sparse (in tufts), white<br>SC: moderate to numerous<br>DFP: present; pale yellow-brown<br>SMP: yellow-brown to brown |
| Peptone-Yeast Extract Iron Agar (ISP 6) | G: fair<br>AM: present; sparse, white<br>SC: absent<br>DFP: present; pale yellow-brown<br>SMP: yellow-brown to brown |
| AV Agar | G: fair<br>AM: present; sparse, white to yellow-brown<br>SC: numerous<br>DFP: present; pale yellow-brown<br>SMP: Rust brown (CHM 5pg) |
| Gauze's Mineral Agar I | G: fair to good<br>AM: present; sparse, white<br>SC: moderate<br>DFP: absent<br>SMP: pale yellow-brown to brown |
| ATCC Medium 172 | G: excellent<br>AM: present; sparse to moderate, white to ivory (CHM 2db)<br>SC: moderate<br>DFP: present; yellow-brown<br>SMP: deep brown (CHM 6pl) |
| Czapek-Sucrose Agar | G: poor<br>AM: present; sparse to moderate, white<br>SC: numerous<br>DFP: absent<br>SMP: translucent, off-white |
| Glucose-Yeast Extract Agar | G: excellent<br>AM: present; sparse, white<br>SC: sparse to numerous<br>DFP: yellow-brown<br>SMP: moderate brown (ISCC-NBS 58) |

TABLE 1-continued

Macroscopic Appearance of *Actinomadura fulva* susp. indica SCC 1840, ATCC 53714 on various descriptive media[a]

| MEDIUM | RESULT |
|---|---|
| | to dark brown (ISCC-NBS 59) |

[a]G = growth; AM = aerial mycelium; SC = spore chain; DFP = diffusible pigment; SMP = substrate mycelium pigmentation

FERMENTATION OF THE MICROORGANISM

The antimicrobial complex 530 of this invention is produced when the elaborating microorganism, *Actinomadura fulva* subsp. *indica* SCC 1840, ATCC 53714 is grown in an aqueous nutrient medium under submerged aerobic conditions at a temperature of about 27° C. to 40° C., preferably at from 27° C. to 35° C., and at a pH of from about 6.5 to 8.0 with agitation until substantial antimicrobial activity is imparted to the medium. Temperature studies indicate that the organism grows rapidly at about 30° C. Therefore, the fermentation is preferably conducted employing a single temperature pattern of 30° C. for a period of about 24 to about 96 hours preferably about 90 hours. The fermentation is generally conducted from about 3 to 7 days, preferably for about 3 days.

To determine when peak antimicrobial production has been reached, samples of the fermentation broth were assayed every 24 hours (starting at 48 hrs.) for antimicrobial content by bioassay of the whole broth against *Staphylococcus aureus* ATCC 209P (pH 8.0), *Escherichia coli* ATCC 10536 (pH 8.0) and *Candida albicans* Wisconsin. The growth of the organism (packed cell volume), pH and dissolved oxygen levels are determined either intermittantly or continuously.

As nutrient medium, there is employed any suitable medium containing a source of carbon, for example an assimilable carbohydrate, and a source of nitrogen, for example an assimilable nitrogenous or proteinaceous material and various mineral salts.

The medium employed for the fermentation contained meat peptone SB (an enzymatic hydrolysate of casein) and soluble starch as the major sources of nitrogen and carbon, respectively. Under these conditions, the microorganism, SCC 1840, produced antimicrobial complex 530 containing at least one biologically active component as determined by bioautography against both *S. aureus*, *E. coli* and *C. abicans* of the complex after development of a thin layer chromatography plate in 2:2:1 (v/v/v) chlorofrom: methanol: pH 3.5 acetate buffer.

The foregoing media are exemplary of the nutrients utilized by *Actinomadura fulva* subsp. *indica* to produce antimicrobial complex 530. However, it is obvious to those trained in the fermentation science that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from 6.5 to 8.0, a pH of from 6.5 to 7.5 being preferred. Prior to sterilization, the pH of the medium is usually adjusted to 6.7 and prior to inoculation, the pH is usually adjusted to 7.0.

The fermentation was initiated by addition of the inoculum to the broth. Generally, inoculum volume is 2.5% of total broth volume. The inoculum is prepared by addition of a sample of the frozen whole broth to an appropriate medium. A particularly preferred medium comprises beef extract, 0.3%; tryptone, 0.5%; cerelose, 0.1% potato starch, 2.4%; yeast extract, 0.5%; and calcium carbonate, 0.2% (all percents by weight). The pH of the inoculum medium is adjusted to 7.5 prior to sterilization. The inoculum stage of the fermentation usually requires from 24 to 120 hours with 2 to 4 days preferred and is generally conducted at about 30° C. with agitation. Agitation and a positive air flow, generally about 3.5 L/min. and a temperature of about 30° C. are employed during tank fermentations.

ISOLATION AND PURIFICATION OF THE ANTIMICROBIAL COMPLEX 530

The antimicrobial complex 530 of this invention contains a complex mixture of antimicrobials, including as the major component, the compound represented by formula 1, a macrolactam disaccharide along with several minor components. The antimicrobial complex 530 of this invention is isolated by extraction of the whole fermentation broth with n-butanol. The n-butanol extract is concentrated, dissolved in chloroform:methanol (1:1 v/v) and the so formed mixture is added to ether:hexane (6:4 v/v). The so-formed precipitate is the antimicrobial complex of this invention which exhibits antifungal activity against Candida spp. and antibacterial activity against gram positive and negative bacteria.

ISOLATION AND PURIFICATION OF THE COMPOUND OF THIS INVENTION (Formula 1)

The antimicrobial complex 530 of this invention was subjected to preparative High Performance Liquid Chromatography (HPLC) on silica gel using chloroform:methanol (95:5 v/v) as the eluting solvent to produce a mixture of macrolactam monosaccharides and the compound represented by formula 1 which was further purified by using counter-current chromatography with a mobile phase of chloroform:methanol:water (7:10:8 v/v; lower phase). The compound represented by formula 1 was recovered in substantially chemically pure form from the lower phase. The compound represented by formula 1 is an unstable compound and breaks down to form a macrolactam monosaccharide having the formula

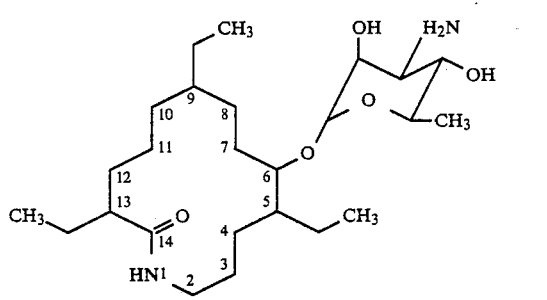

The FAB mass spectrum of the compound represented by formula 1 shows a molecular ion peak at 619 (M+H); high resolution mass measurements reveal the molecular formula of the compound of formula 1 to be $C_{31}H_{58}N_2O_{10}$. The compound represented by formula 1 was stabilized by conversion to the hexaacetate derivative. The physiochemical data for the more stable hexaacetate derivative are given in Table II.

TABLE II

| PHYSIOCHEMICAL DATA FOR HEXAACETATE | |
|---|---|
| UV(MeOH) λmax (nm) | End Absorption |
| IR(KBr) $v_{max}$(cm − 1) | 3320, 2930, 1750, 1655, 1540, 1375, 1230, 1050. |
| FAB Mass Spec. | 871(M + H), 541 |
| $^1$H NMR(CDCl$_3$) | 5.5(m, 2H), 5.1(t, J=8 Hz, 1H) 4.93(t, J=8 Hz, 1H), 4.7(m, 4H), 4.15(dd, J=8 Hz, 1H), 4.05(d, J=8 Hz, 1H), 3.92(dd, J=6, 4 8, 1 Hz, 1H), 3.75(dt, J=6,4 Hz, 1H), 3.5(m, 4H), 3.1(bt, J=12 Hz, 1H), 3.0(bd, J=12 Hz, 1H), 2.05(s, 3H), 2.0(s, 6H), 1.96(s, 3H), 1.94(s, 3H), 1.92(s, 3H), 0.9-1.6(m, 26H), 0.7-0.9(m, 9H). |

The $^{13}$C NMR chemical shifts of the hexaacetate represented by formula 2 (R=COCH$_3$) are given in Table III.

TABLE III

| | Carbon-13 NMR Shifts[a,b] Hexacetate formula 2 |
|---|---|
| —CH$_3$ | 9.10 |
| | 12.46 |
| | 12.66 |
| CH$_2$ | 20.79 |
| | 22.49 |
| | 23.12 |
| | 25.06 |
| | 25.27 |
| | 26.77 |
| | 27.25 |
| | 28.23 |
| | 31.78 |
| | 33.73 |
| | 38.66 |
| CH | 38.85 |
| | 40.89 |
| | 50.89 |
| | 77.93 |
| O‖C | 175.85 |
| SUGAR I | 94.06 |
| | 73.25 |
| | 72.43 |
| | 67.00 |
| | 55.15 |
| | 17.76 |
| CO<u>C</u>H$_3$ | 20.79 |
| | 20.79 |
| | 20.79 |
| | 20.79 |
| | 21.20 |
| | 21.66 |
| <u>C</u>OCH$_3$ | 169.36 |
| | 169.69 |
| | 169.99 |
| | 170.15 |
| | 170.20 |
| | 170.61 |
| SUGAR II | 89.97 |
| | 74.35 |
| | 72.89 |
| | 71.09 |
| | 68.63 |

TABLE III-continued

Carbon-13 NMR Shifts[a,b]
Hexacetate
formula 2

61.96

[a] all shifts in PPM.
[b] CDCl$_3$ was used as solvent.

Based on the analysis of mass spectral data on the compound represented by formula 1 and the physicochemical data on the hexaacetate derivative and comparison of the $^{13}$C-NMR data for the hexacetate derivative of the compound of formula 1, the structure of the compound isolated from antimicrobial complex 530 produced by fermentation of A. fulva subsp. indica ATCC 53714 was shown to be that of formula 1, a macrolactam disaccharide.

THE BIOLOGICAL ACTIVITY OF THE ANTIMICROBIAL COMPLEX 530, THE COMPOUNDS OF FORMULAS 1 AND 2

The antimicrobial complex 530 of this invention exhibits both antifungal activity and antibacterial activity in vitro against Gram positive and Gram negative microorganisms.

The compound represented by formula 1, isolated from the antimicrobial complex 530-exhibits in vitro antifungal in a Sabouraud dextrose broth medium against eight species of Candida (geometric mean MIC of 19 mcg/mL) and seven species of dermatophytes (geometric mean MIC of 71 mcg/mL).

The hexacetate derivative, i.e., compound represented by formula 2 wherein R=CH$_3$CO—, exhibits in vitro antibacterial activity against Gram positive and Gram negative microorganisms, e.g., S. aureus ATCC 209 P, E. coli ATCC 10536, Pseudomonas 720 72401 and Sarcilutia ATCC 9341.

PHARMACEUTICAL COMPOSITIONS

This invention also contemplates antimicrobially effective pharmaceutical compositions comprising an antimicrobially effective amount of a compound of formula 1 or pharmaceutically acceptable salts thereof in admixture with a pharmaceutically acceptable, non-toxic carrier adapted for topical, oral or parenteral use.

The preferred pharmaceutically acceptable salts are nontoxic acid addition salts formed by adding to the compounds of the present invention about a stoichiometric amount of a mineral acid, such as HCl, HBr, H$_2$SO$_4$ or H$_3$PO$_4$, or of an organic acid, such as acetic, propionic, valeric, oleic, palmitic, stearic, lauric, benzoic, lactic, para-toluene sulfonic, methane sulfonic, citric, maleic, fumaric, succinic and the like.

The topical, oral and parenteral dosage forms may be prepared according to procedures well known in the art, and may contain a variety of ingredients.

In the case of topical formulations, e.g., ointments, creams, lotions, powders, tablets, pessaries or sprays, the formulation will contain about 0.1 to 10 grams of a compound of formula 1 per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and may contain salts or glucose to make the solution isotonic.

In general, the dosage of compound of formula 1 administered to combat a given microbial infection is similar to the dosage requirements of the present commercial products miconazole, clotrimazole, and ketoconazole.

In general, the topical dosage range of the compound of formula 1 is from about 0.1% to about 10% by weight of a particular pharmaceutical composition formulated in single or divided doses, with the preferred range being about 0.5% to about 4% and with the most preferred range being about 1% to about 2%.

In general, the oral dosage for humans of the compound of formula 1 administered to combat a given microbial infection ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans of the compound of formula 1 administered to combat a given microbial infection ranges for about 0.1 mg per kilogram of body weight per day, to about 20 mg per kilogram of body weight per day, in single or divided doses, with about 1 mg per kilogram of body weight per day being preferred.

It will be appreciated that the actual preferred dosages of the compound of this invention or pharmaceutically acceptable salts thereof will vary according to the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

The following examples illustrate the invention:

EXAMPLE 1

Preparation of the Antimicrobial Complex 530 of This Invention

A. Inoculum Preparation (1) Initial Stage

Prepare a 250 mL Erlemneyer flask with 70 mL of the following germination medium:

| | |
|---|---|
| Beef Extract | 3 g |
| Tryptone | 5 g |
| Yeast Extract | 5 g |
| Cerelose | 1 g |
| Potato Starch | 24 g |
| Calcium Carbonate | 2 g |
| Tap Water | 1000 mL |
| AF-1* | 1 mL |

*AF-1 is an antifoam agent available from Dow Corning Corp., Midland, MI 48641.

Adjust the pH of the germination broth to 7.5. Sterilization the broth and after cooling, add 3.5 mL of a frozen whole broth sample of the microorganism of this invention from a previously prepared inoculum to each flask broth. Incubate at 30° C. with continual agitation of 300 rpm for 48 hours.

(2) Second Stage

Transfer 25 mL of the first stage germination broth to each of twenty 2-liter Erlenmeyer flasks, each containing 500 mL of the same germination medium and which had been previously pH adjusted and sterilized. Incubate at 30° C. with continual agitation at 300 rpm for 48 hours.

B. Fermentation

In a 2 L fermentor, add 350 ml of the following medium:

| | |
|---|---|
| Cerelose | 25.0 g |
| Soluble Starch | 5.0 g |
| Pro Flo Flour | 10.0 g |
| Marcor Meat Peptone SB | 5.0 g |
| Sodium Nitrate | 1.0 g |
| $ZnSO_4 \cdot 7H_2O$ 5% solution | 1.0 ml |
| $MgCl_2 \cdot 6H_2O$ | 0.5 g |
| $FeSO_4 \cdot 7H_2O$ 1.4% solution | 1.0 ml |
| Tap $H_2O$ | 1000.0 ml |
| Antifoam (AF-1 Dow Corning) | 0.5 ml |

Adjust the pH of the medium to 7.9 and then sterilize the medium. After sterilization, adjust the pH of the medium to 7.0 with a sterile acidic solution. Inoculate the fermentation medium with 25 mL of the second stage inoculum preparation of Step A. Incubate the fermentation mixture at 30° C. with a positive air flow and 300 rpm agitation for about 90 hours.

C. Isolation

Extract 5.5 L of the fermentation broth two times with equal volumes of n-butanol. Combine the n-butanol solutions, dry over anhydrous sodium sulfate, filter and concentrate by evaporation under reduced pressure. Dissolve the concentrate in 50 mL of chloroform:methanol (1:1 v/v) and then add this solution to 2 liters of ether:hexane (6:4 v/v) until a precipitate results (4.08 g). Filter the precipitate and separate the macrolactam monosaccharides from the compound of formula 1 by preparative HPLC on a silica gel cartridge using $CHCl_3$; $CH_3OH$ (95:5, v/v) as the developing solvent. The active fractions containing macrolactam disaccharide were combined and the solvent was removed therefrom to provide 765 mg of an active complex. The active complex 530 (57 mg) was placed on an ITO Multicoil Counter Current Chromatographic instrument using the lower phase of the solvent mixture $CHCl_3:CH_3OH:H_2O$ (7:10:8, v/v/v) as the mobile phase and the upper phase as the stationary phase. The active fractions were identified by TLC and combined. The compound of formula 1 shows a white lipid-like spot on TLC plates sprayed with water. The solvent was removed from the active fractions to provide 6.2 mg of the compound represented by formula I in substantially chemically pure form. FAB mass spectrum showed a molecular ion peak at 619 (M+H). The molecular formula, $C_{31}H_{58}N_2O_{10}$ was determined by analysis of the high resolution mass spectrum measurements.

EXAMPLE 2

Preparation of the Hexaacetate

Acetylate the compound of Example 1 in a stirred mixture of 1:1.5 acetic anhydride-pyridine at 0° C. for 3 hours. Stir the reaction mixture overnight at room temperature. Quench the reaction mixture in ice and extract the so-formed mixture with an equal volume of ethyl acetate. Wash the organic extract with dilute HCl and brine. Dry same over anhydrous sodium sulfate to give a crude solid. Chromatograph the crude solid on a silica gel column, eluting with a mixture of ethyl acetate:hexane:methanol (50:50:1.5, v/v/v) to give the pure hexaacetate of formula 2, $R=CH_3CO-$. The physiochemical data for the hexaacetate is provided in Tables II and III.

By substituting the appropriate alkanoic anhydride or alkenoic anhydride for acetic anhydride, the compounds of formula 2 wherein R is straight or branched chain ($C_1-C_{22}$) alkanoyl or straight or branched chain ($C_3-C_{22}$) alkenoyl are formed.

What is claimed is:

1. The compound represented by the formula 1:

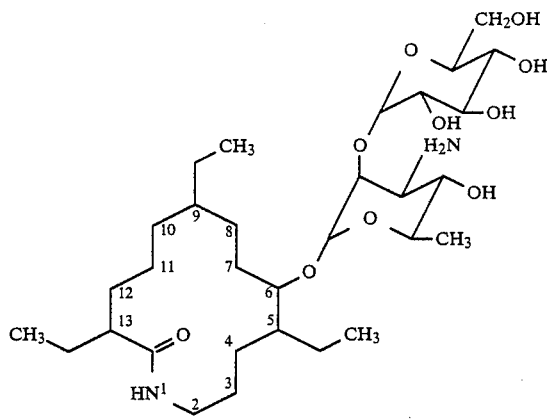

in substantially chemically pure form, or a pharmaceutically acceptable salt thereof.

2. A pharmaceutical composition comprising an antimicrobially effective amount of the compound of claim 1 and a pharmaceutically acceptable carrier or diluent.

3. The pharmaceutical composition of claim 2 suitable for parenteral administration.

4. The pharmaceutical composition of claim 2 suitable for topical administration.

5. The pharmaceutical composition of claim 2 suitable for oral administration.

6. A method for treating a bacterial infection in a host having a susceptible bacterial infection which comprises administering to said host an antibacterially effective amount of the compound of claim 1 or a pharmaceutical composition thereof.

7. The method of claim 6 wherein the route of administration is parenteral.

8. The method of claim 6 wherein the route of administration is topical.

9. The method of claim 6 wherein the route of administration is oral.

10. A compound represented by the formula 2:

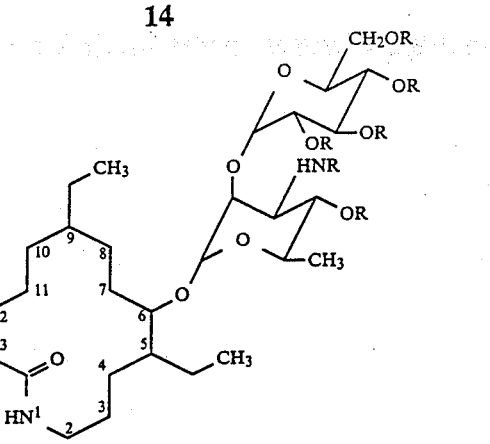

wherein R is a straight or branched chain ($C_1$–$C_{22}$) alkanoyl group, a straight or branched chain ($C_3$–$C_{22}$) alkenoyl group or hydrogen with the proviso that at least one R is not hydrogen or a pharmaceutically acceptable salt thereof.

11. A compound of claim 10 wherein R is a straight or branched chain ($C_1$–$C_{22}$) alkanoyl group.

12. A compound of claim 10 wherein R is a straight or branched chain ($C_3$–$C_{22}$) alkenoyl group.

* * * * *